United States Patent
Tabbara et al.

(10) Patent No.: US 7,184,819 B2
(45) Date of Patent: Feb. 27, 2007

(54) USER INTERFACE SYSTEM FOR USE IN ECG SIGNAL DERIVATION AND MANAGEMENT

(75) Inventors: Besher Tabbara, Saugus, MA (US); Paul E. Gilman, Gloucester, MA (US)

(73) Assignee: Draeger Medical Systems, Inc., Andover, MA (US)

( * ) Notice: Subject to any disclaimer, the term of this patent is extended or adjusted under 35 U.S.C. 154(b) by 571 days.

(21) Appl. No.: 10/354,645

(22) Filed: Jan. 30, 2003

(65) Prior Publication Data

US 2004/0024328 A1 Feb. 5, 2004

Related U.S. Application Data

(60) Provisional application No. 60/400,297, filed on Aug. 1, 2002.

(51) Int. Cl.
*A61B 5/044* (2006.01)

(52) U.S. Cl. .................................. 600/523

(58) Field of Classification Search ............... 600/523, 600/516, 517; 345/700
See application file for complete search history.

(56) References Cited

U.S. PATENT DOCUMENTS

| | | | |
|---|---|---|---|
| 4,850,370 A | 7/1989 | Dower | 128/699 |
| 5,058,598 A | 10/1991 | Nicklas et al. | 128/699 |
| 5,318,037 A | 6/1994 | Evans et al. | 128/696 |
| 5,377,687 A | 1/1995 | Evans et al. | 128/700 |
| 5,566,096 A * | 10/1996 | Wodlinger et al. | 702/191 |

(Continued)

OTHER PUBLICATIONS

U.S. Appl. No. 10/286,020, filed Nov. 2, 2002, B. Tabbara et al.
U.S. Appl. No. 09/844,443, filed Mar. 3, 2001, Simon H. Meij et al.
U.S. Appl. No. 09/922,170, filed Apr. 27, 2001, Simon H. Meij.

(Continued)

*Primary Examiner*—Scott M. Getzow
(74) *Attorney, Agent, or Firm*—Jack Schwartz, PLLC

(57) ABSTRACT

The system provides a Graphical User Interface which automatically updates labels associated with waveform information in multiple different windows within an individual image and in different images for use in a medical information telemetry system in synthesis and non-synthesis modes. A user interface display system for use in ECG signal management includes a display generator for generating at least one display image enabling assignment of two measured ECG chest lead signals to any two signals of the six ECG chest lead signals of a conventional 12 lead ECG signal set. A command processor automatically updates labels associated with the six ECG chest lead signals displayed in a display image to be compatible with the assignment of the two measured ECG chest lead signals in response to an assignment command made via the at least one display image.

22 Claims, 20 Drawing Sheets

U.S. PATENT DOCUMENTS

| | | | |
|---|---|---|---|
| 5,711,304 A | 1/1998 | Dower | 128/696 |
| 5,743,859 A * | 4/1998 | Wodlinger et al. | 600/522 |
| 6,119,035 A | 9/2000 | Wang | 600/509 |
| 6,188,407 B1 * | 2/2001 | Smith et al. | 715/841 |
| 6,217,525 B1 | 4/2001 | Medema et al. | 600/508 |
| 6,931,271 B2 * | 8/2005 | Tabbara et al. | 600/509 |
| 2002/0013518 A1 | 1/2002 | West et al. | 600/300 |
| 2002/0035334 A1 | 3/2002 | Meij et al. | 600/509 |
| 2002/0045837 A1 | 4/2002 | Wei et al. | 600/509 |

OTHER PUBLICATIONS

U.S. Appl. No. 10/286,020, filed Nov. 1, 2002, Copending B. Tabbara et al.

Scherer, J.A. et al. "Synthesis of the 12 lead electrocardiogram from a 3 lead semi-orthogonal subset using patient-specific linear transformation arrays" Computers in Cardiology 1988; IEEE comput. Soc. PR. US, Sep. 25, 1988, pp. 449-451.

* cited by examiner

FIGURE 3

$$\begin{bmatrix} \text{Derived Chest 1} \\ \text{Derived Chest 2} \\ \text{Derived Chest 3} \\ \text{Derived Chest 4} \end{bmatrix} = \begin{bmatrix} C0,0 & C0,1 & C0,2 & C0,3 \\ C1,0 & C1,1 & C1,2 & C1,3 \\ C2,0 & C2,1 & C2,2 & C2,3 \\ C3,0 & C3,1 & C3,2 & C3,3 \end{bmatrix} * \begin{bmatrix} \text{Lead I} \\ \text{Lead II} \\ \text{Lead V} \\ \text{Lead V+} \end{bmatrix}$$

*Derived Chest 1* = C0,0 * *Lead I* + C0,1 * *Lead II* + C0,2 * *Lead V* + C0,3 * *Lead V+*

*Derived Chest 2* = C1,0 * *Lead I* + C1,1 * *Lead II* + C1,2 * *Lead V* + C1,3 * *Lead V+*

*Derived Chest 3* = C2,0 * *Lead I* + C2,1 * *Lead II* + C2,2 * *Lead V* + C2,3 * *Lead V+*

*Derived Chest 4* = C3,0 * *Lead I* + C3,1 * *Lead II* + C3,2 * *Lead V* + C3,3 * *Lead V+*

Figure 4a

Matrix Coefficients

Coefficient Matrix for lead combination V1V2

{{0.124276, 0.528647, -0.470581, 0.959203},
{0.366777, 0.646839, -0.419272, 0.439137},
{0.243609, 0.612888, -0.240065, 0.063791},
{0.051211, 0.525849, -0.166559, -0.064981}}

Coefficient Matrix for lead combination V1V3

{{0.451028, -0.106476, 1.164328, 0.374929},
{0.173483, 0.300353, -0.362114, 0.614655},
{0.134774, 0.500708, -0.325473, 0.182146},
{0.002947, 0.518251, -0.264215, -0.002567}}

Coefficient Matrix for lead combination V1V4

{{0.604678, -0.029586, 1.479829, 0.243511},
{0.252270, 0.047158, 0.784046, 0.871991},
{-0.086674, 0.241251, -0.280170, 0.536497},
{-0.139528, 0.375958, -0.317945, 0.198076}

Coefficient Matrix for lead combination V1V5

{{0.754809, 0.095972, 1.553465, 0.075997},
{0.706900, 0.320721, 1.087822, 0.555162},
{0.370100, -0.007219, 0.421460, 1.152623},
{-0.172038, 0.150020, -0.183337, 0.589238}}

Coefficient Matrix for lead combination V1V6

{{0.777195, 0.219323, 1.503403, -0.147286},
{0.869673, 0.673735, 1.005209, -0.014885},
{0.707447, 0.291534, 0.474198, 0.809631},
{0.292379, 0.042956, 0.157448, 1.121053}}

Coefficient Matrix for lead combination V2V1

Coefficient Matrix for lead combination V2V3

{{-0.464470, -0.075641, 0.599723, -0.094743},
{0.320585, 0.282038, -0.288053, 0.711130},
{0.270397, 0.491627, -0.247459, 0.258820},
{0.116903, 0.519243, -0.187913, 0.048300}}

Coefficient Matrix for lead combination V2V4

{{-0.448599, -0.070791, 0.551284, -0.086612},
{-0.061269, 0.078345, 0.551089, 0.729656},
{0.027627, 0.235239, -0.189888, 0.582952},
{-0.006967, 0.375606, -0.206621, 0.245240}}

Coefficient Matrix for lead combination V2V5

{{-0.463263, -0.069138, 0.526381, -0.096909},
{0.170326, 0.256123, 0.741823, 0.518945},
{0.161941, -0.032158, 0.288818, 1.139168},
{-0.083482, 0.161517, -0.115293, 0.599321}}

Coefficient Matrix for lead combination V2V6

{{-0.481182, -0.061058, 0.512799, -0.128770},
{0.333948, 0.488976, 0.737081, 0.185473},
{0.452568, 0.199263, 0.356895, 0.917815},
{0.209198, 0.015749, 0.112339, 1.147806}}

Coefficient Matrix for lead combination V3V1

{{0.451028, -0.106476, 0.374929, 1.164328},
{0.173483, 0.300353, 0.614655, -0.362114},
{0.134774, 0.500708, 0.182146, -0.325473},
{0.002947, 0.518251, -0.002567, -0.264215}}

Coefficient Matrix for lead combination V3V2

{{-0.464470, -0.075641, -0.094743, 0.599723},
{0.320585, 0.282038, 0.711130, -0.288053},
{0.270397, 0.491627, 0.258820, -0.247459},
{0.116903, 0.519243, 0.048300, -0.187913}}

Coefficient Matrix for lead combination V3V4

Coefficient Matrix for lead combination V3V5

{{-0.502252, -0.196114, 0.448307, -0.408821},
{-0.089912, -0.251821, 0.902233, -0.603456},
{0.086140, -0.138222, 0.419610, 0.930599},
{-0.060330, 0.199103, -0.144826, 0.677692}}

Coefficient Matrix for lead combination V3V6

{{-0.546441, -0.104891, 0.366195, -0.558147},
{-0.164332, -0.151235, 0.787226, -0.770679},
{0.250726, -0.108707, 0.563376, 0.900174},
{0.147061, -0.078712, 0.174577, 1.139741}}

Coefficient Matrix for lead combination V4V1

{{0.604678, -0.029586, 0.243511, 1.479829},
{0.252270, 0.047158, 0.871991, 0.784046},
{-0.086674, 0.241251, 0.536497, -0.280170},
{-0.139528, 0.375958, 0.198076, -0.317945}}

Coefficient Matrix for lead combination V4V2

{{-0.448599, -0.070791, -0.086612, 0.551284},
{-0.061269, 0.078345, 0.729656, 0.551089},
{0.027627, 0.235239, 0.582952, -0.189888},
{-0.006967, 0.375606, 0.245240, -0.206621}}

Coefficient Matrix for lead combination V4V3

{{-0.478807, -0.273412, -0.403873, 0.616398},
{-0.044100, -0.353020, -0.623730, 1.162994},
{0.008301, 0.264660, 0.826313, -0.337073},
{-0.020283, 0.418091, 0.475264, -0.334412}}

Coefficient Matrix for lead combination V4V5

{{-0.528643, -0.063602, 0.766770, -1.095094},
{-0.144672, 0.015245, 1.550726, -1.992338},
{-0.089780, 0.302724, 1.852411, -1.675843},
{-0.029554, 0.151155, -0.349946, 1.003786}}

Coefficient Matrix for lead combination V4V6

Coefficient Matrix for lead combination V5V1

{{0.754809, 0.095972, 0.075997, 1.553465},
{0.706900, 0.320721, 0.555162, 1.087822},
{0.370100, -0.007219, 1.152623, 0.421460},
{-0.172038, 0.150020, 0.589238, -0.183337}}

Coefficient Matrix for lead combination V5V2

{{-0.463263, -0.069138, -0.096909, 0.526381},
{0.170326, 0.256123, 0.518945, 0.741823},
{0.161941, -0.032158, 1.139168, 0.288818},
{-0.083482, 0.161517, 0.599321, -0.115293}}

Coefficient Matrix for lead combination V5V3

{{-0.502252, -0.196114, -0.408821, 0.448307},
{-0.089912, -0.251821, -0.603456, 0.902233},
{0.086140, -0.138222, 0.930599, 0.419610},
{-0.060330, 0.199103, 0.677692, -0.144826}}

Coefficient Matrix for lead combination V5V4

{{-0.528643, -0.063602, -1.095094, 0.766770},
{-0.144672, 0.015245, -1.992338, 1.550726},
{-0.089780, 0.302724, -1.675843, 1.852411},
{-0.029554, 0.151155, 1.003786, -0.349946}}

Coefficient Matrix for lead combination V5V6

{{-0.530938, 0.167892, 0.722339, -1.600257},
{-0.121147, 0.438455, 1.510999, -2.969914},
{-0.010904, 0.727218, 2.198549, -3.067394},
{0.040145, 0.233045, 2.106434, -1.678931}}

Coefficient Matrix for lead combination V6V1

{{0.777195, 0.219323, -0.147286, 1.503403},
{0.869673, 0.673735, -0.014885, 1.005209},
{0.707447, 0.291534, 0.809631, 0.474198},
{0.292379, 0.042956, 1.121053, 0.157448}}

Coefficient Matrix for lead combination V6V2

Coefficient Matrix for lead combination V6V3

{{-0.546441, -0.104891, -0.558147, 0.366195},
{-0.164332, -0.151235, -0.770679, 0.787226},
{0.250726, -0.108707, 0.900174, 0.563376},
{0.147061, -0.078712, 1.139741, 0.174577}}

Coefficient Matrix for lead combination V6V4

{{-0.564006, 0.073655, -1.038431, 0.378905},
{-0.213630, 0.224033, -1.811486, 0.836061},
{-0.155770, 0.407584, -1.389274, 1.235699},
{0.038798, -0.067708, 0.838759, 0.366871}}

Coefficient Matrix for lead combination V6V5

{{-0.530938, 0.167892, -1.600257, 0.722339},
{-0.121147, 0.438455, -2.969914, 1.510999},
{-0.010904, 0.727218, -3.067394, 2.198549},
{0.040145, 0.233045, -1.678931, 2.106434}}

470

470   472

USER INTERFACE SYSTEM FOR USE IN ECG SIGNAL DERIVATION AND MANAGEMENT

This is a non-provisional application of provisional application Ser. No. 60/400,297 by B. Tabbara et al. filed Aug. 1, 2002.

FIELD OF THE INVENTION

The present invention relates to electrocardiogram (ECG) systems and in particular to a user interface system for use in ECG signal synthesis and management.

BACKGROUND OF THE INVENTION

ECG systems are well known, and provide information about the physiological status of a patient's heart to a physician. More specifically, so called conventional 12 lead ECG systems exist which provide twelve waveforms, called leads (lead signals), to a physician. To provide such a 12 lead ECG, ten electrodes are placed on the patient's body, and the signals from these electrodes are processed to provide twelve lead signals in a known manner. These ten electrodes include four electrodes which provide signals that are processed to generate six limb lead signals, and six electrodes which provide signals that are processed to provide precordial or chest leads.

However, there are conditions under which it is preferable or expedient to attach a limited number, (e.g. two), chest lead electrodes to a patient and to synthesize (predict) the remaining (e.g., four) chest lead signals of the six chest lead signals of the 12 lead ECG set. Such conditions include, for example, when one or more of the six standard chest lead locations on the patient's body, at which one or more of the electrodes should be placed, may be unavailable due to injury or surgery. Alternatively, it may be desirable to save time (e.g., in an emergency) to attach just two of the six standard chest lead electrodes or there may be one or more chest lead signals giving intermittent or degraded response for which it may be desirable to substitute synthesized signals. In some cases, patient comfort or the use of telemetered ECG signals may render it desirable to monitor patients with a reduced number of chest electrodes, while producing a full set of six chest lead signals. It is desirable under these conditions to still provide the full set of 6 chest lead signals by synthesizing the remaining chest lead signals of the 12 lead ECG set. under these conditions to still provide the full set of 6 chest lead signals by synthesizing the remaining chest lead signals of the 12 lead ECG set.

It is known that the signals representing the respective ECG lead signals contain mutually redundant information. It is also known that, should one electrode be missing or malfunctioning, an appropriate combination of signals from the other electrodes and/or the other leads, which are available and functional, may be used to generate a synthesized signal which closely approximates the lead signal derived from the missing or malfunctioning electrode. To apply this technique, at least some portion of a full 12 lead ECG is recorded, during an analysis phase. The recorded signals are then processed to generate a function, which may be applied to the lead signals which are available, to synthesize a lead signal which approximates the lead signal which is missing or distorted beyond use. During a synthesis phase, this function is then applied to the available ECG lead signals. Using this technique, a missing lead may be synthesized. However the technique involves the disadvantages of being relatively complex and time consuming to perform. It is desirable to provide an ECG chest lead signal synthesis and user interface system that is capable of enabling a user to simply and relatively quickly synthesize chest lead signals.

BRIEF SUMMARY OF THE INVENTION

The system provides a Graphical User Interface which automatically updates labels associated with waveform information in multiple different windows within an individual image and in different images for use in a medical information telemetry system when supporting multiple modes associated with different numbers of ECG lead signals. A user interface display system for use in ECG signal management includes a display generator for generating at least one display image enabling assignment of two measured ECG chest lead signals to any two signals of the six ECG chest lead signals of a conventional 12 lead ECG signal set. A command processor automatically updates labels associated with the six ECG chest lead signals displayed in a display image to be compatible with the assignment of the two measured ECG chest lead signals in response to an assignment command made via the at least one display image.

BRIEF DESCRIPTION OF THE DRAWING

In the drawing:

FIG. 3 is a diagram illustrating a transformation for synthesizing ECG chest lead signals, according to principles of the present invention.

FIGS. 4a–4e show patient non-specific coefficients for use in the transformation of FIG. 3, according to principles of the present invention.

DETAILED DESCRIPTION OF THE INVENTION

Figure 1:
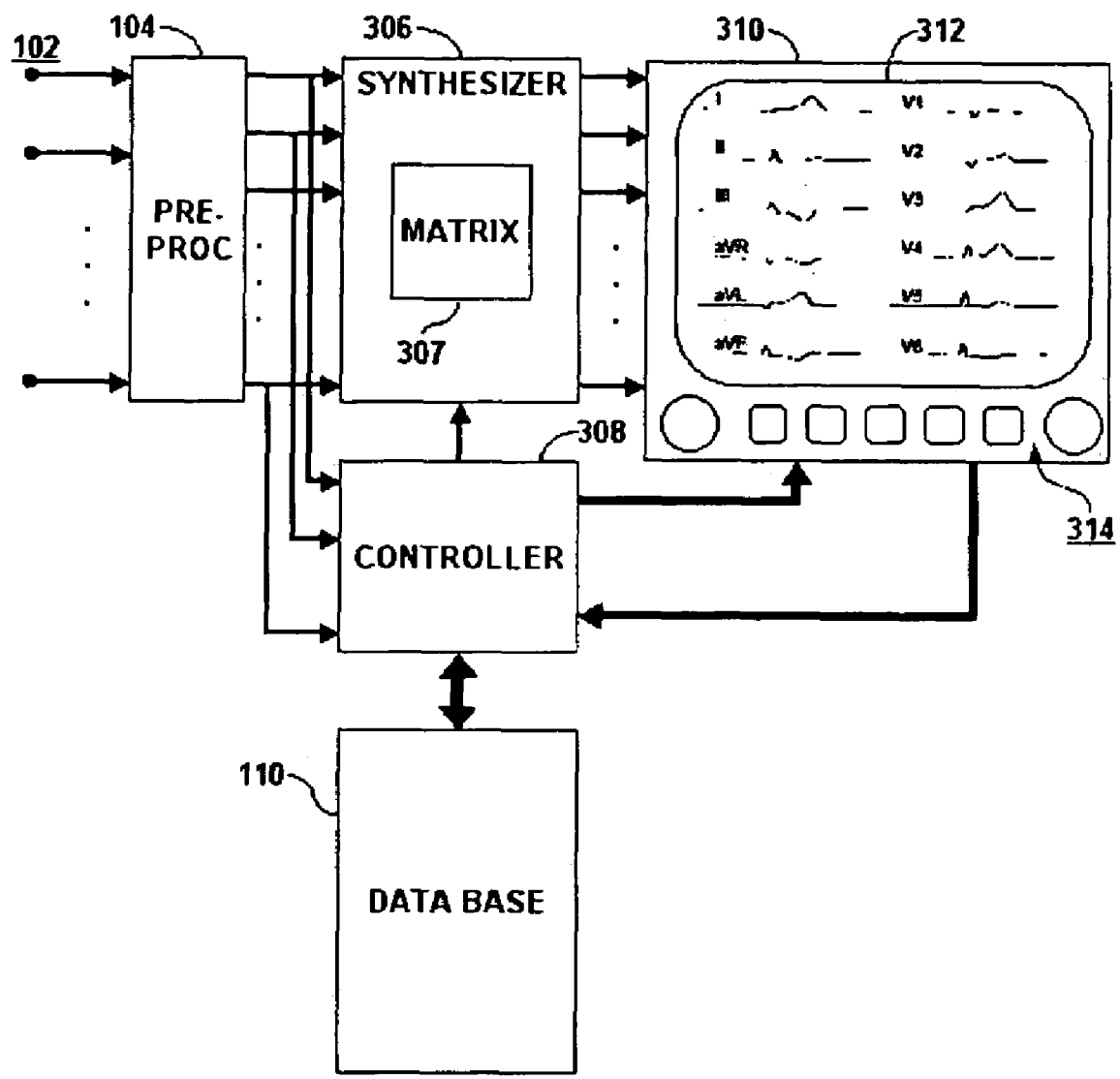
FIG. 1 is a diagram showing an ECG synthesis system in a patient monitoring device, according to principles of the present invention.

The system provides a Graphical User Interface in which a user is not constrained to have to update waveform information manually in multiple screens that are in a medical information telemetry system when switching between the multiple modes associated with different numbers of ECG lead signals. FIG. 1 is a diagram showing an ECG synthesis system in a patient monitoring device. In FIG. 1, a plurality 102 of electrodes are intended to be attached to respective locations on a patient's body. The plurality 102 of electrodes are coupled to respective input terminals of a preprocessor 104. Respective output terminals of the preprocessor 104 are coupled to corresponding input terminals of synthesizer 306 and controller 308. Respective output terminals of the synthesizer 306 are coupled to corresponding data input terminals of a display device 310. A synthesizer control output terminal of controller 308 is coupled to a control input terminal of the synthesizer 306, and a display device control output terminal of the controller 308 is coupled to a control input terminal of the display device 310. The display device includes a display screen 312 and a set of user controls 314. These user controls 314 may include, among other controls, knobs, illustrated as circles, and buttons, illustrated as rounded squares. A user control output terminal of the display device 310 is coupled to a user control input terminal of the controller 308. A bidirectional terminal of the controller 308 is coupled to a corresponding terminal of the database 110.

In operation, the plurality of electrodes 102 are ECG electrodes which are intended to be attached to predetermined locations on a patient. In the illustrated embodiment, the plurality of electrodes 102 comprise six electrodes including Left Arm (LA), Right Arm (RA), Left Leg (LL), Right Leg (RL), Chest electrode 1 (lead signal V), and Chest Electrode 2 (lead signal V+). The electrode signals are wirelessly transmitted to preprocessor 104 using known telemetry techniques. In contrast, the conventional 12-Lead ECG set employs 10 electrodes including the four limb electrodes LA, RA, LL, RL and six chest electrodes V1, V2, V3, V4, V5, and V6 and these are used to provide 12 conventional ECG lead signals labeled I, II, III, aVR, aVL, aVF, V1, V2, V3, V4, V5, and V6 as known. Lead signals I and II are computed from LA, RA, LL, and RL electrode raw data and in turn signals I and II are used to mathematically derive III, aAR, aVL, and aVF as known. In the illustrated embodiment, the derivation of the limb lead signals is not germane to the present invention and they are not discussed in the remainder of this application.

The system presented herein advantageously adaptively derives up to four ECG chest lead signals of a conventional 12 lead ECG signal set from two measured ECG chest lead signals coupled to two of the standard chest lead electrode positions (i.e., two of the standard V1, V2, V3, V4, V5, and V6 electrode positions). The system advantageously does this for any patient based on predetermined stored data without requiring the accumulation and analysis of ECG data of a particular patient for use in synthesizing patient specific chest lead signal data. In the FIG. 1 system the six input electrodes 102 comprising signals LA, RA, LL, RL, V (chest electrode 1 lead signal), and V+ (Chest Electrode 2 lead signal) are advantageously used to provide the conventional 12 lead ECG signal set (comprising lead signals identified as I, II, III, aVR, aVL, aVF, V1, V2, V3, V4, V5, and V6).

In the illustrated embodiment of FIG. 1, preprocessor 104 includes analog to digital converters to convert the six input analog electrode signals to multi-bit digital form. Preprocessor 104 further processes the digitized ECG signal data to identify characteristics of each ECG complex and to time align and aggregate (e.g. average, median filter, etc.) some number of successive ECG complexes for each lead, in a known manner. An individual ECG complex comprises signal data occupying a predetermined time period and bandwidth received from a patient attached electrode. Digital data representing the six, optionally averaged, input ECG lead complexes is stored, in a known manner, in respective locations in memory in synthesizer 306. Synthesizer 306, controller 308 and database 110 together process the input ECG lead complexes stored in unit 306 memory to provide data representing ECG waveforms for display on display screen 312 of display device 310.

As illustrated in FIG. 1, the display device 310 displays the 12 lead ECG waveforms from the synthesizer 306 on the display screen 312 in the usual manner for ECG waveforms. In addition, the controller 308 can respond to user input from the user controls 314 on the display device 310, and can condition the display device 310 to display information on the display screen 312. Controller 308 also controls the operation of synthesizer 306 in response to the lead signals from the preprocessor 104, in a manner to be described in detail below. Synthesizer 306 processes the six input electrode signals 102 (LA, RA, LL, RL, V and V+) to provide the conventional 12 lead ECG signal set (I, II, III, aVR, aVL, aVF, V1, V2, V3, V4, V5, and V6) including up to four synthesized chest lead signals, for display on device 310.

The plurality of electrodes 102 are attached to predetermined locations on a patient by a user. Two of the leads (corresponding to leads V and V+) are attached to two of the six chest electrodes located in the six standard positions, V1, V2, V3, V4, V5, and V6 in the conventional 12 lead ECG signal set as previously described. In response to a user selecting two of the six chest electrodes in the standard positions as measurement electrode lead signals V and V+, synthesizer 306 calculates the remaining four chest lead signals. In operation, a user connects the two measurement chest leads V and V+ to chest electrodes at positions V1 and V2 on a patient, for example. The user employs user controls 314 on display device 310 to enter information concerning the monitoring desired, including, e.g., information identifying the patient being measured. The user also employs user controls 314 to select a chest lead identification image window and to associate the two measurement chest leads V and V+ with chest electrodes V1 and V2.

If the user fails to associate the two measurement chest leads V and V+ with any chest electrodes and associated lead labels, the system operates in a passthrough mode. In this mode controller 308 detects that chest leads V and V+ have not been associated with any chest electrodes and conditions the synthesizer 306 to pass the V and V+ lead signals through to the output without change. In this mode synthesizer 306 operation is disabled for the particular patient concerned and synthesizer 306 does not derive any of the remaining four chest lead signals V3, V4, V5, and V6. Instead, the two measurement chest leads V and V+ waveforms and associated V and V+ labels are displayed on screen 312. If the user associates the two measurement chest leads V and V+ with incorrect chest electrodes and associated lead labels, the system may display invalid data.

Figure 5:
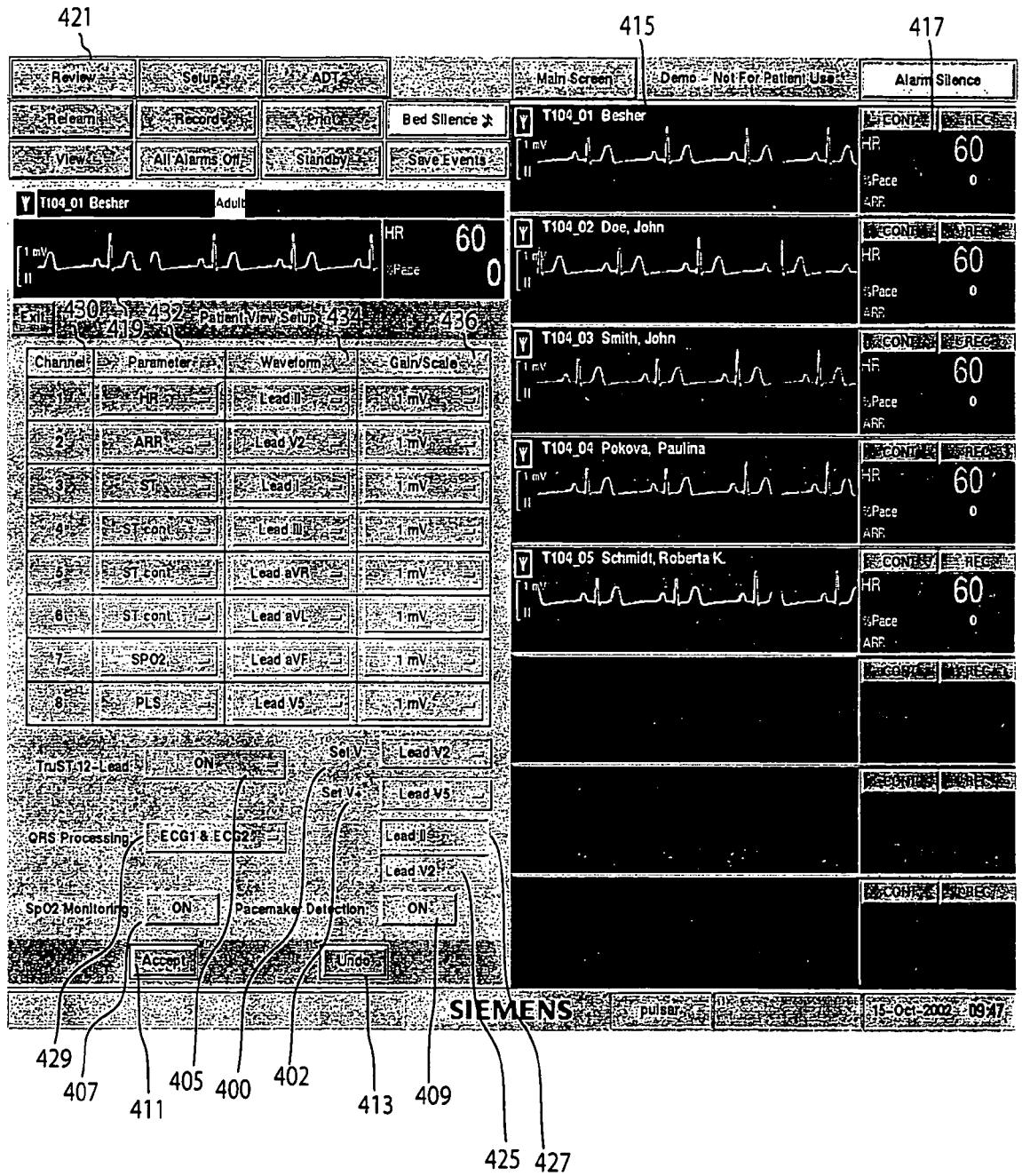
FIGS. 5–16 show user interface display images supporting operation of an ECG signal processing and display system and incorporating automatically updated ECG signal associated labels responsive to user signal assignment commands made via a display image, according to principles of the present invention.

FIGS. 5–16 show user interface display images supporting operation of an ECG signal processing and display system and incorporating automatically updated ECG signal associated labels responsive to user signal assignment commands made via a display image. Specifically, the user interface system automatically and dynamically updates ECG signal associated labels in multiple different waveform and parameter display images, windows and associated menus (exemplified in FIGS. 5–16) used for set-up and waveform and parameter display. This is done in response to user association of the two measurement chest leads V and V+ with particular chest electrodes via the displayed windows. The user interface display image of FIG. 5 supports user selection of a particular order of display of particular ECG waveforms of the conventional 12 lead ECG signal set in a set up mode. A user is able to allocate a particular ECG waveform 434 to a particular display channel 430 to be displayed with a particular user selectable parameter label 432 and user selectable gain or scale 436. The display image of FIG. 5 illustrates, in window 415, display of channel 1 showing conventional ECG set Lead II for five patients of a particular bed station together with a corresponding parameter box (e.g., box 417) identifying the waveform as indicating HR (Heart Rate). The single waveform illustrated in display area 419 replicates the top waveform of window 415. Further, the display options 421 allow a user to navigate to other display images supporting other display and set up functions. The display image of FIG. 5 also illustrates user association of the two measurement chest leads V and V+ with chest electrodes V2 and V5 via items 400 and 402 (set V and set V+) respectively. Upon initialization in a synthesis mode, the system also defaults to a particular electrode selection that is alterable by a user. The synthesis mode is selected to be on or off using item 405 and set up changes made via the display image of FIG. 5 are accepted or undone using items 411 and 413 respectively. The FIG. 5 item 405 indicates synthesis mode is active. The user interface display image of FIG. 5 also enables user selection of additional operational modes. Specifically, a blood oxygen saturation (SpO2) tracking and monitoring mode and a pacemaker detection mode are initiated for the patients associated with channels 1–8 using items 407 and 409 respectively. Item 429 is used to select signals associated with either channel 1 alone or channels 1 and 2 for processing to detect heart rate (HR) and arrhythmia (ARR). In conjunction items 427 and 425 identify the ECG lead signals associated with channels 1 and 2.

Figure 6:
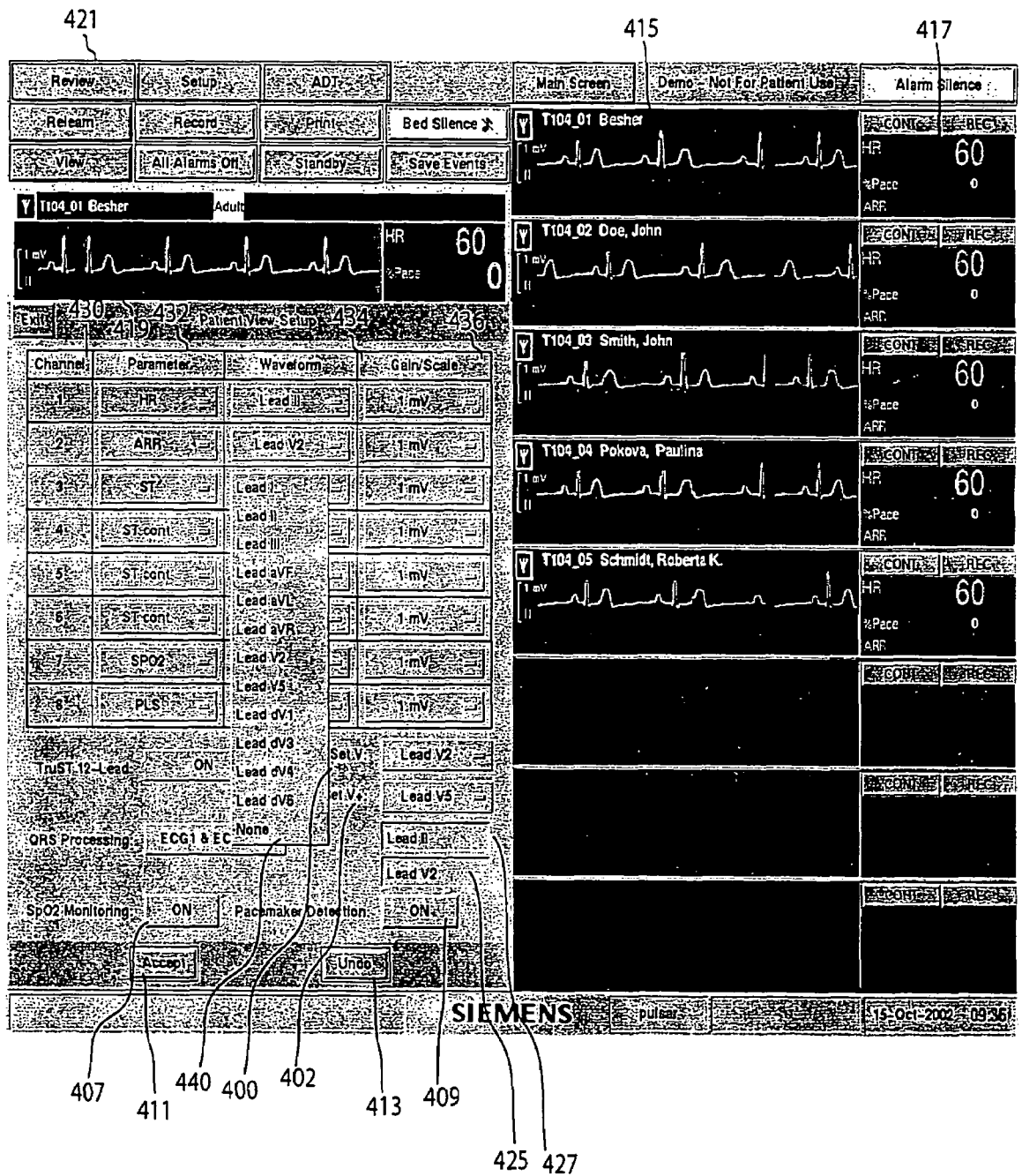

Pop-up menu 440 of the user interface display image of FIG. 6 is displayed in response to user selection of a displayed waveform label in waveform column 434 of the display image of FIGS. 5 and 6. A user employs menu 440 to assign a particular ECG signal lead of the conventional 12 lead ECG signal set to display channel 1–8 of column 430 (specifically channel 3 in the illustrated menu 440 of FIG. 6). Thereby a user selects a particular display order of conventional ECG signal set waveforms in a set up mode. The user interface system advantageously dynamically and automatically updates menu labels in pop-up menu 440 (and other menus) to be compatible with a previous user selection of two measurement chest leads V and V+ with particular chest electrodes (V2 and V5 in the exemplary user interface display images FIGS. 5 and 6). Consequently, pop-up menu 440 offers ECG signal lead labels V2 and V5 indicative of measurement signal lead labels and ECG signal labels dV1, dV3, dV4, and dV6 indicative of the four corresponding derived chest lead signals of the six chest lead signals of a conventional 12 lead ECG signal set. The system assumes that a user has physically placed the chest electrodes on the V2 and V5 location on a patient.

Figure 7:
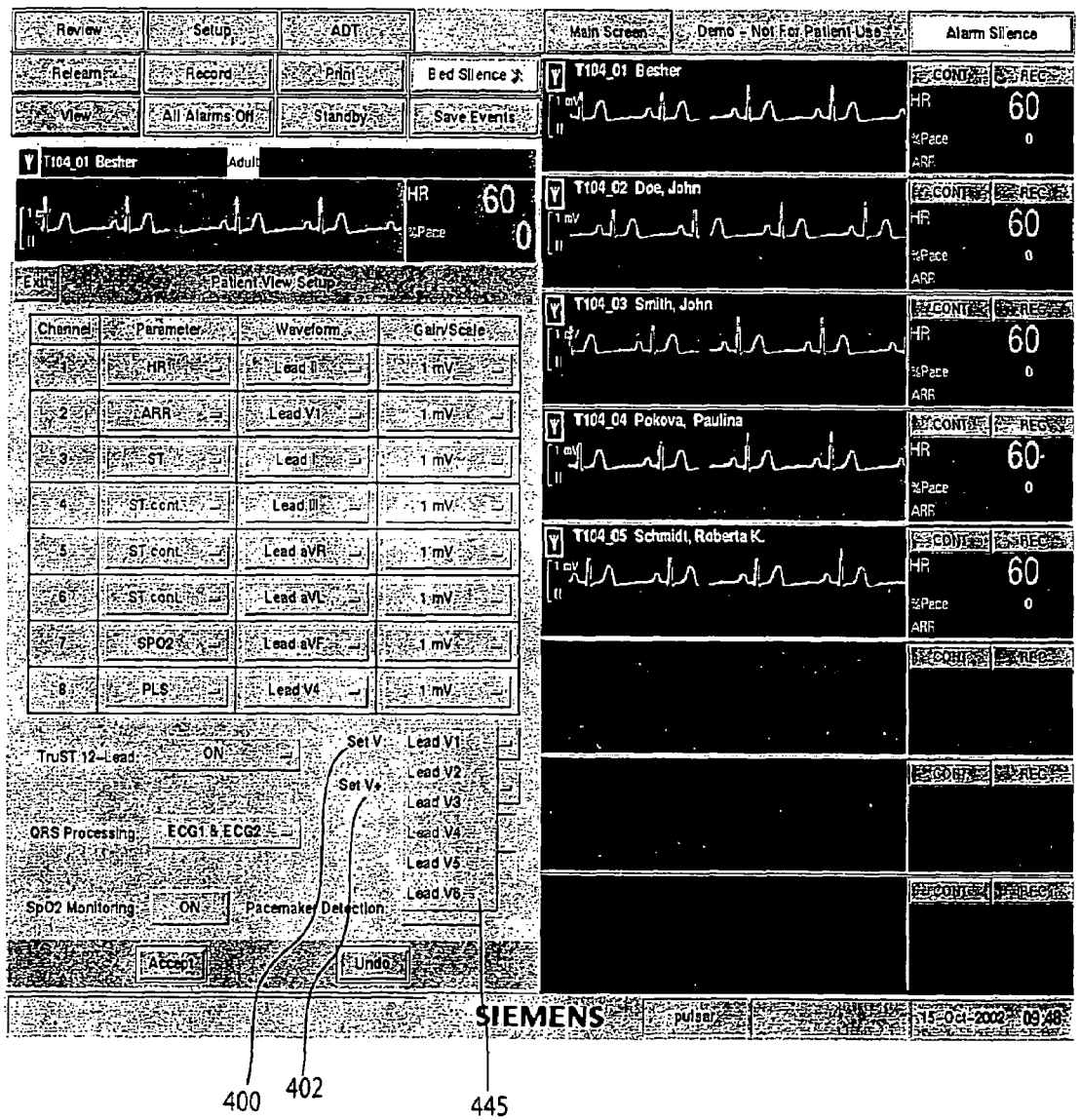
Figure 8:
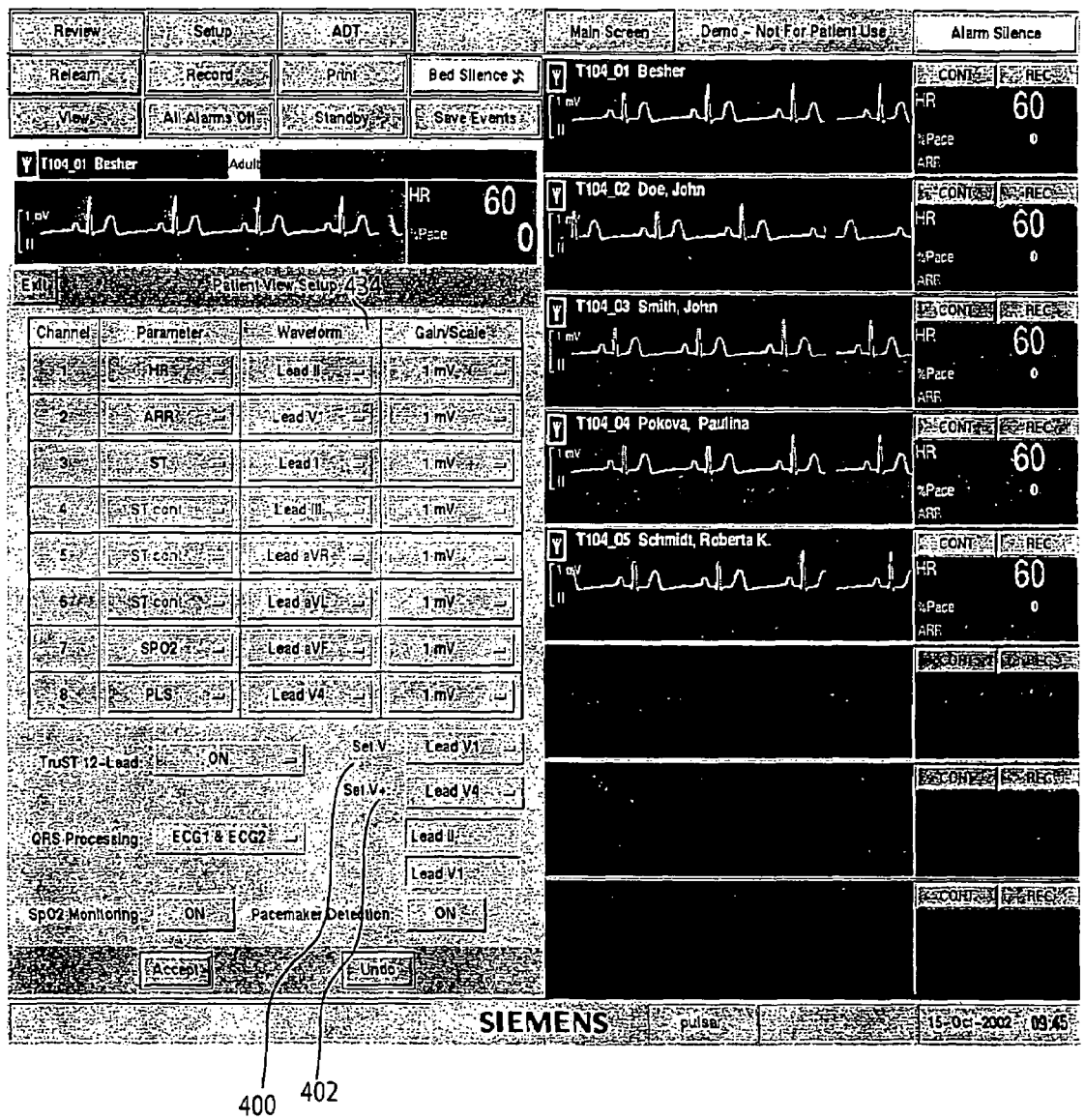

The user interface display image of FIG. 7 illustrates user association of the two measurement chest leads V and V+ with different chest electrodes. In response to a user changing measured ECG chest lead signal assignment via the displayed user interface image (e.g., of FIGS. 5–7) the user interface system automatically updates displayed labels and popup menus to be compatible with the altered assignment. In operation, a user moves the first measurement chest lead position from corresponding location V2 to V1 on a patient and moves the second measurement chest lead position from corresponding location V5 to V4 on the patient. In addition, the user associates the two measurement chest leads V and V+ with the different chest electrodes (e.g., V1 and V4 instead of V2 and V5) via items 400 and 402 (set V and set V+) respectively. In the FIG. 7 image illustration, measurement chest lead V+ is associated by a user with chest electrode V4. Upon user selection of the label list icon associated with set V item 400, pop-up menu 445 is displayed supporting user selection and assignment of the measurement chest lead electrode V with a label shown in menu 445. The labels shown in menu 445 include V1–V3 and V5 and V6. Label V4 is automatically and advantageously excluded (indicated pale in menu 445) by the user interface system since it is already associated with measurement chest lead electrode V+. In response to user assignment of both measurement chest lead electrodes via items 400 and 402, the user interface display system automatically updates image and menu labels and popup menus to be compatible with the altered assignment as shown in the image display of FIG. 8. Specifically, FIG. 8 illustrates updated labels V1 and V4 associated with Set V and Set V+ items 400 and 402 respectively and shows updated waveform labels V1 and V4 associated with channels 2 and 8 (column 434) respectively.

Figure 9:
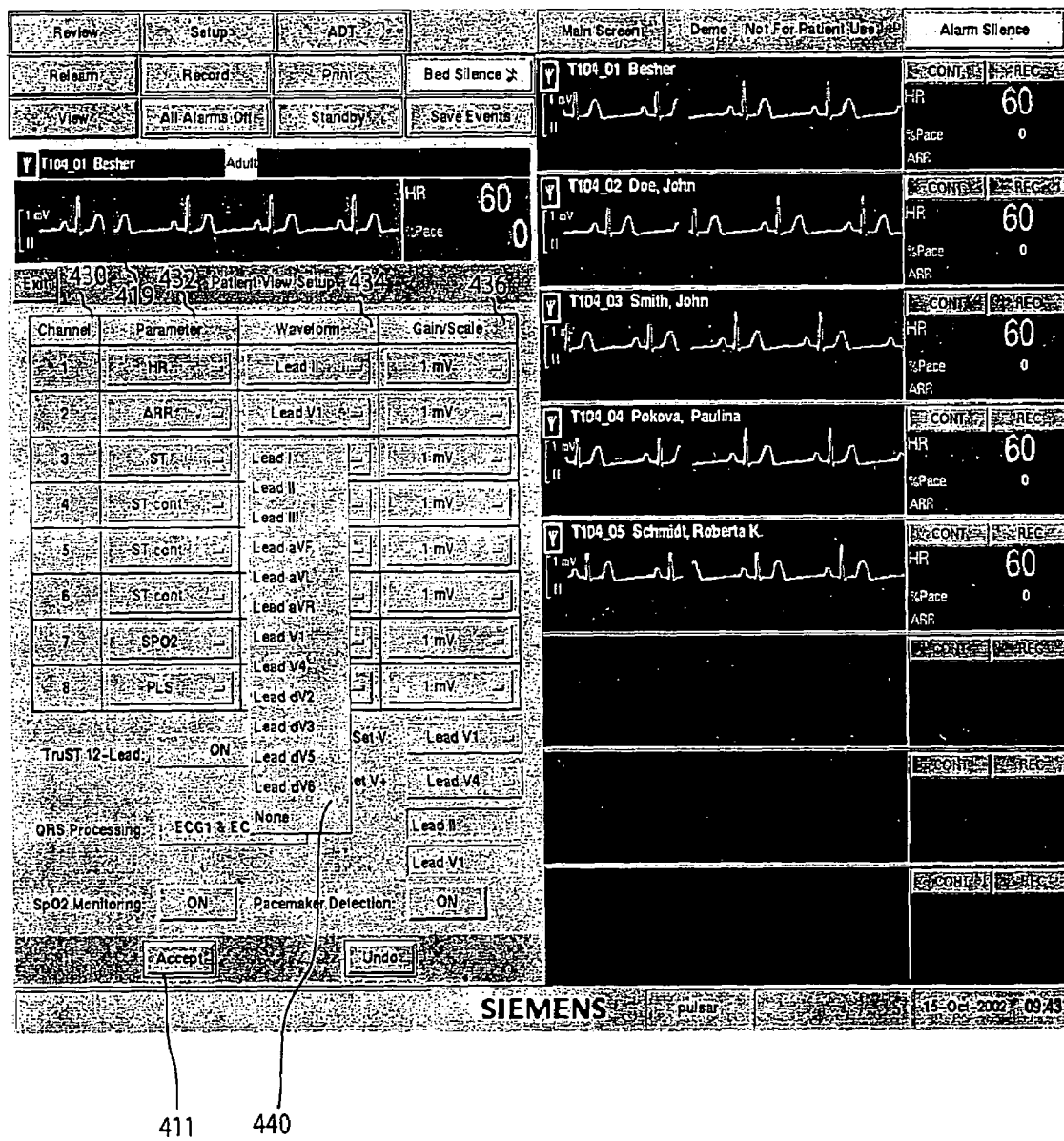
Figure 10:
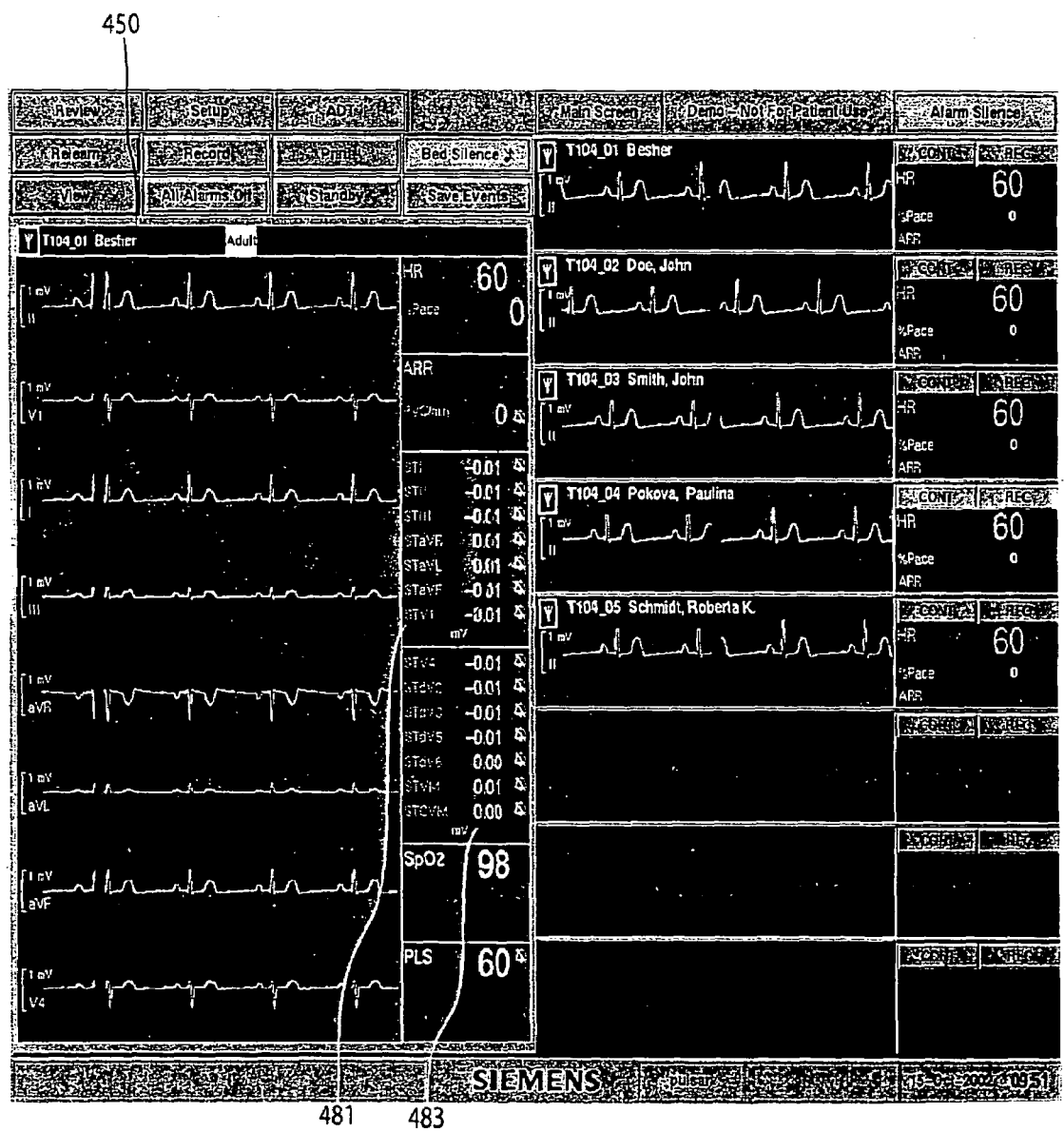

The user interface display image of FIG. 9 illustrates the change in pop-up menu 440 as a result of user association of the two measurement chest leads V and V+ with the different chest electrodes V1 and V4. Specifically, pop-up menu 440 offers ECG signal lead labels V1 and V4 for identifying measurement chest lead signals and ECG signal labels dV2, dV3, dV5, and dV6 for identifying the four corresponding derived chest lead signals of the six chest lead signals of a conventional 12 lead ECG signal set. Upon user assignment of waveform labels to display channels 1–8 (item 430 FIG. 9), the user accepts the settings via activation of item 411. Thereupon, the user is able to select a display image exemplified in FIG. 10 showing the waveforms for a single patient as identified and ordered through selections made via the FIG. 9 user interface display image. The user interface display image of FIG. 10 shows eight signal waveforms (ECG signals II, V1, I, III, aVR, aVL, aVF, V4) for a single particular patient associated with display channels 1–8. These waveforms are displayed in window 450. FIG. 10 also presents windows 481 and 483 displaying 12 ST parameter values of ECG waveform portions related to the S-Wave and T-Wave of an ECG signal complex of individual signals of the 12 signals of the conventional ECG lead signal set. The ST values comprise measurements of elevation or depression in the S-T portion of a given ECG waveform as known. These parameters are commonly used to indicate ischemia, which may lead to a diagnosis of a heart attack, for example. The parameter labels of the 12 ST parameters of windows 481 and 483 are automatically updated to be compatible with a user assignment of the two measurement chest lead electrodes via items 400 and 402. Therefore windows 481 and 483 display labels STV1, STV4, STdV2, STdV3, STdV5 and STdV6 in response to user assignment of the two measurement chest lead electrodes to V1 and V4 via items 400 and 402 (FIG. 7).

Figure 11:
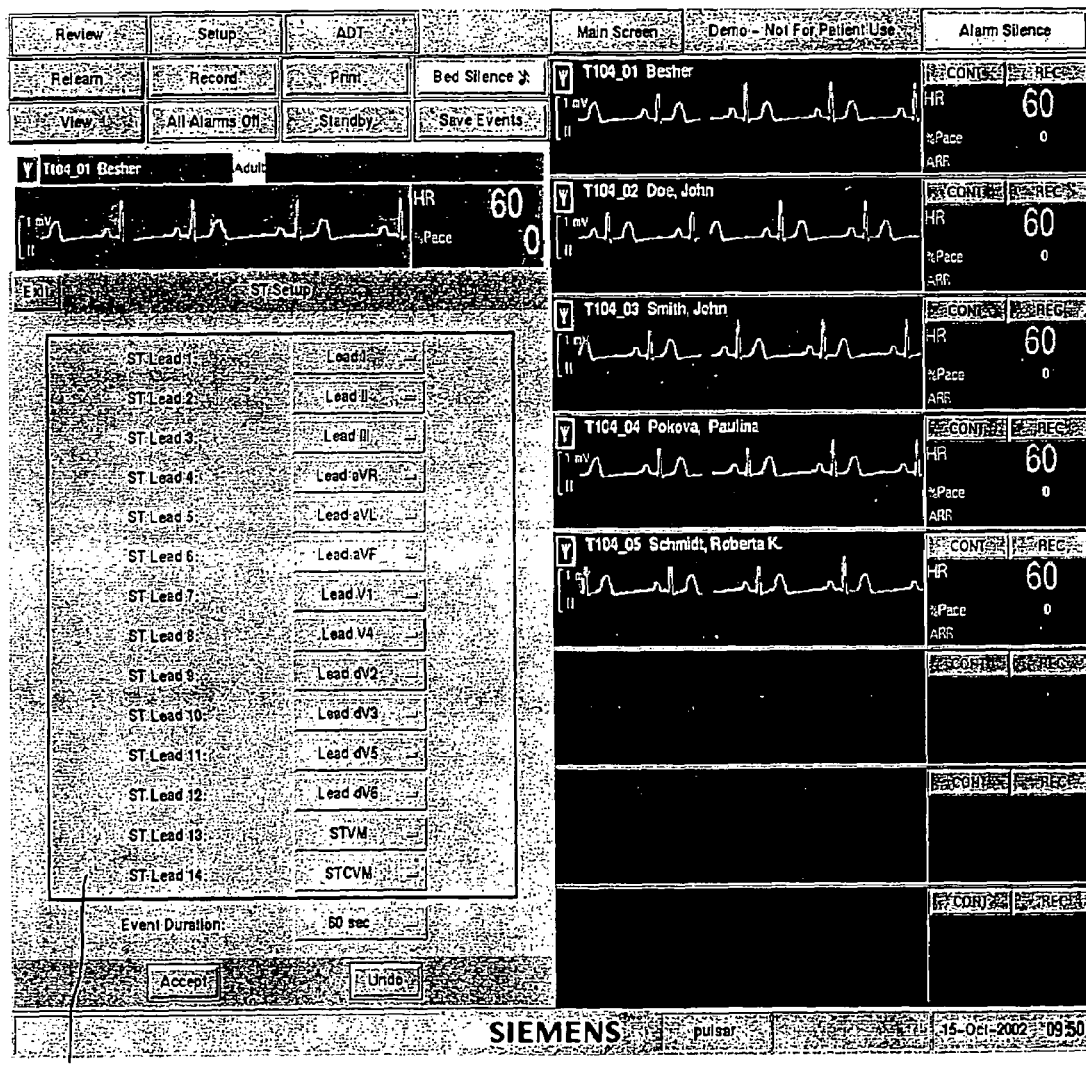
Figure 12:
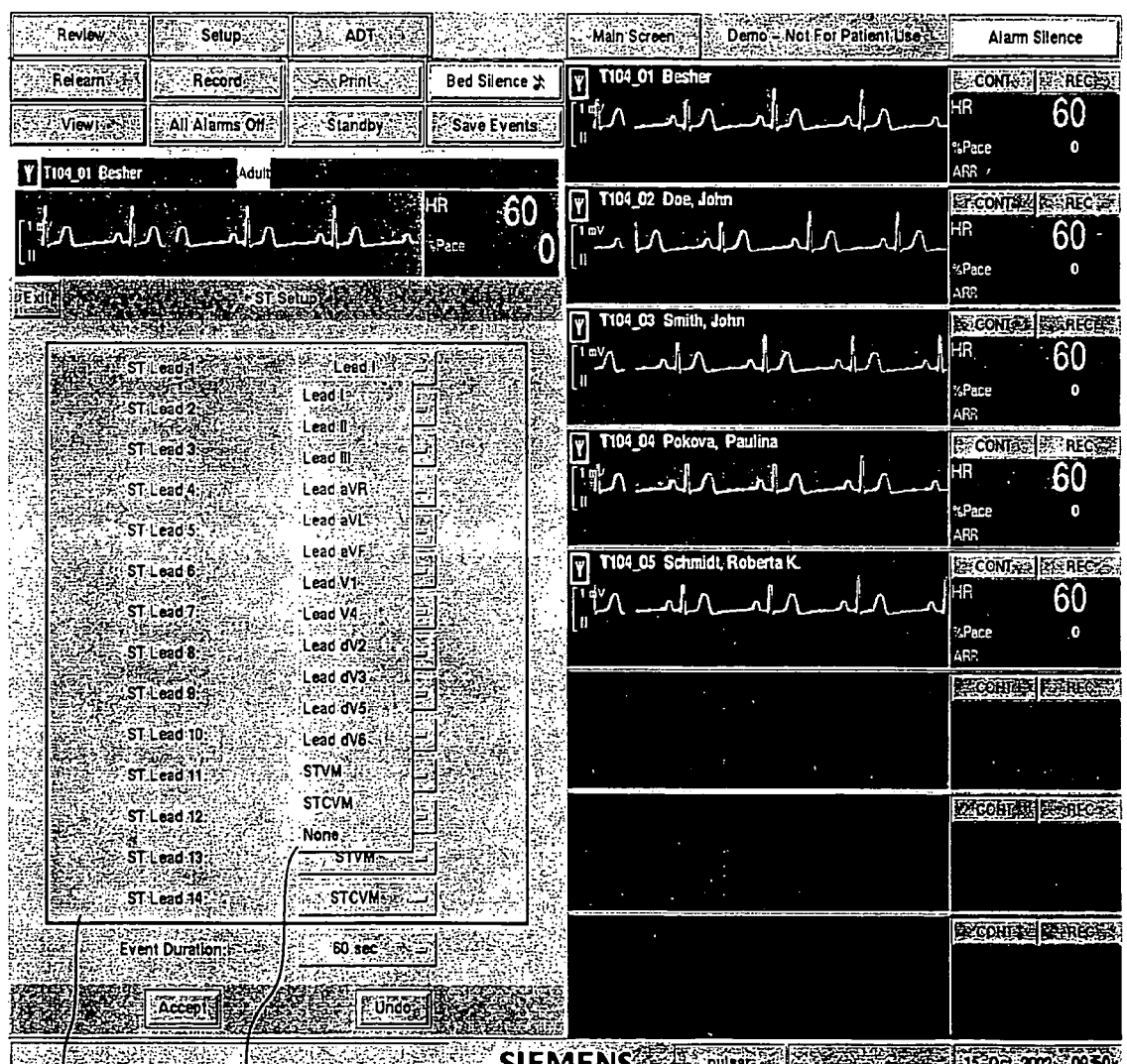

The order of the ST parameters listed inside the windows 481 and 483 of the image of FIG. 10 is set by a user via window 470 of the display image of FIG. 11. Labels identifying ECG lead signals are selectable by a user to associate an individual ECG lead signal with an individual ST parameter via the option menu items of window 470. The selected order of ST parameters in window 470 determines a display order of ST parameters in windows 481 and 483 of FIG. 10. The labels available for user selection via the option menu items of window 470 are automatically updated to be compatible with a user assignment of the two measurement chest lead electrodes via items 400 and 402. Pop-up menu 472 of FIG. 12 illustrates a set of updated labels for use in associating an individual ECG lead signal with an individual ST parameter that is compatible with a user assignment of the two measurement chest lead electrodes via items 400 and 402 (FIG. 5) as shown by V1, V4, dV2, dV3, dV5 and dV6 selection options.

Figure 13:
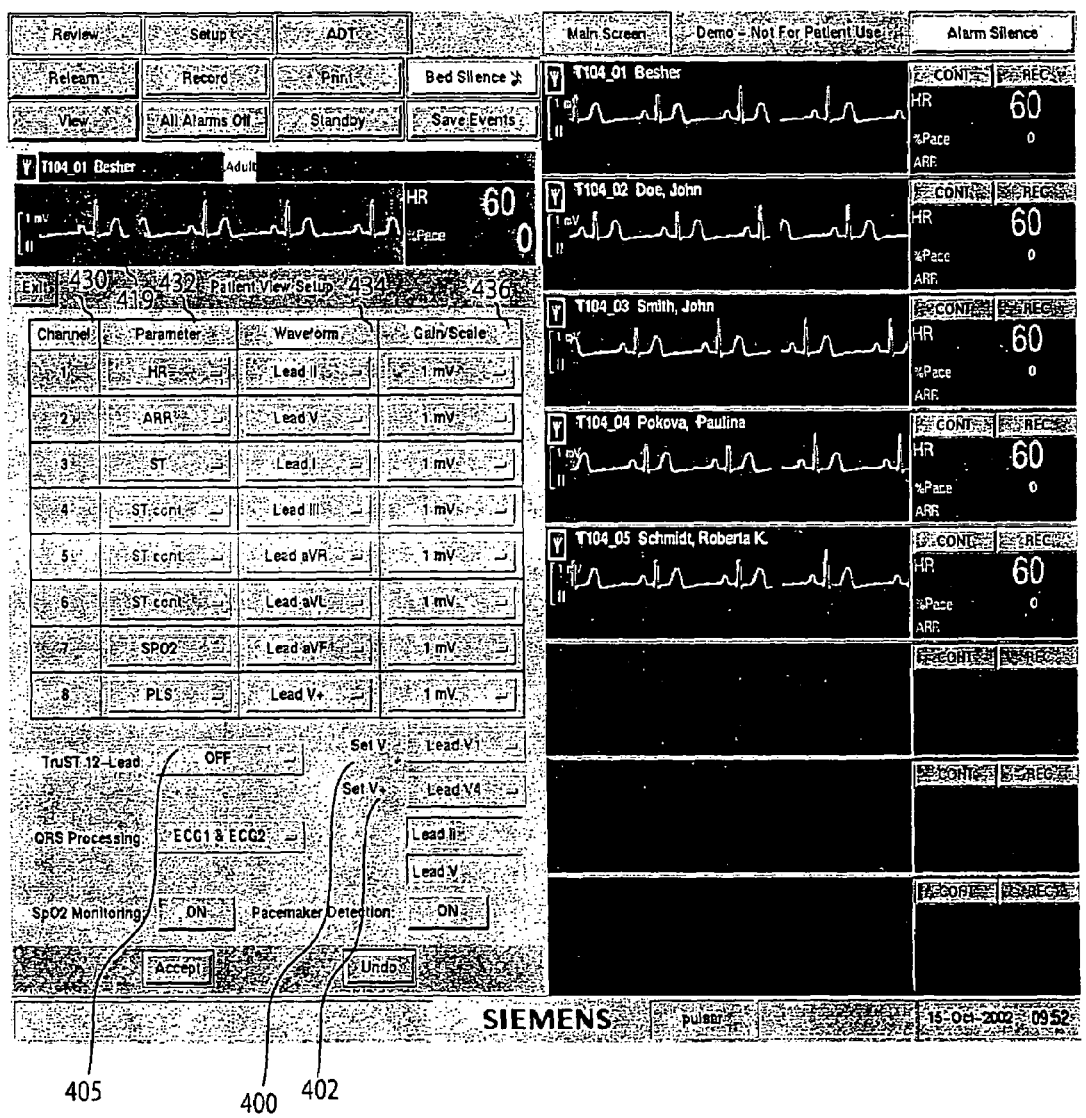
Figure 14:
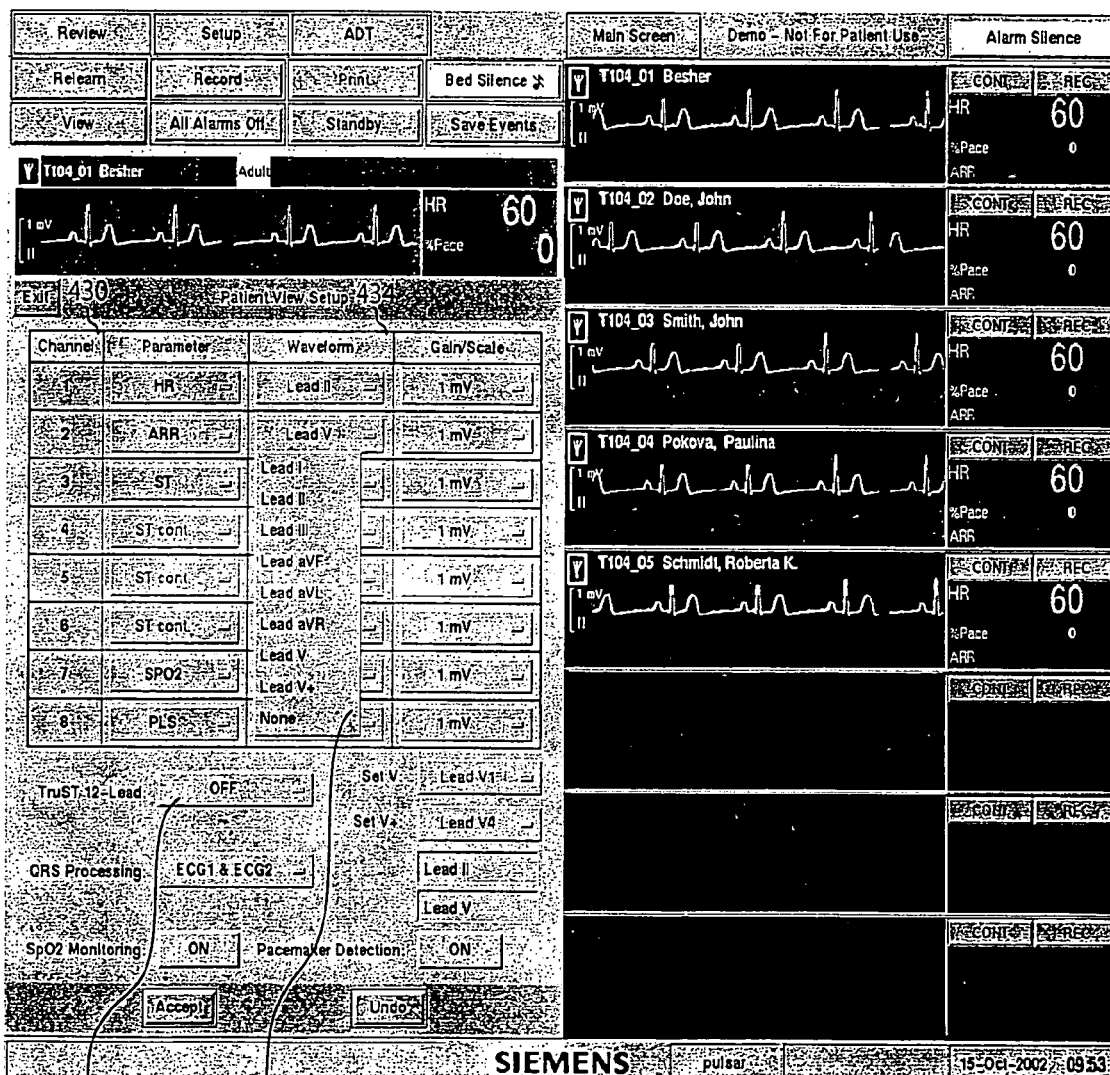
Figure 15:
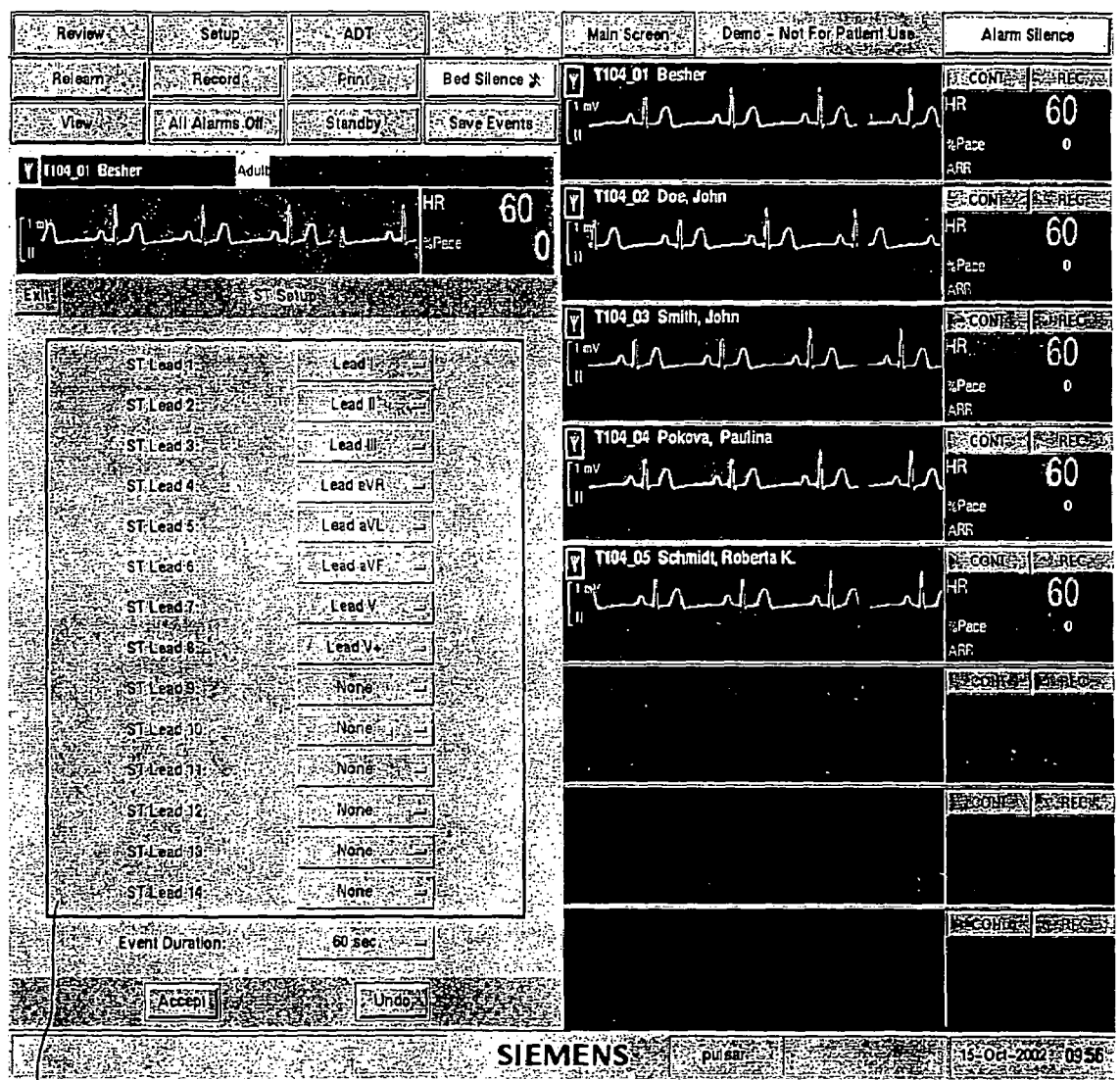
Figure 16:
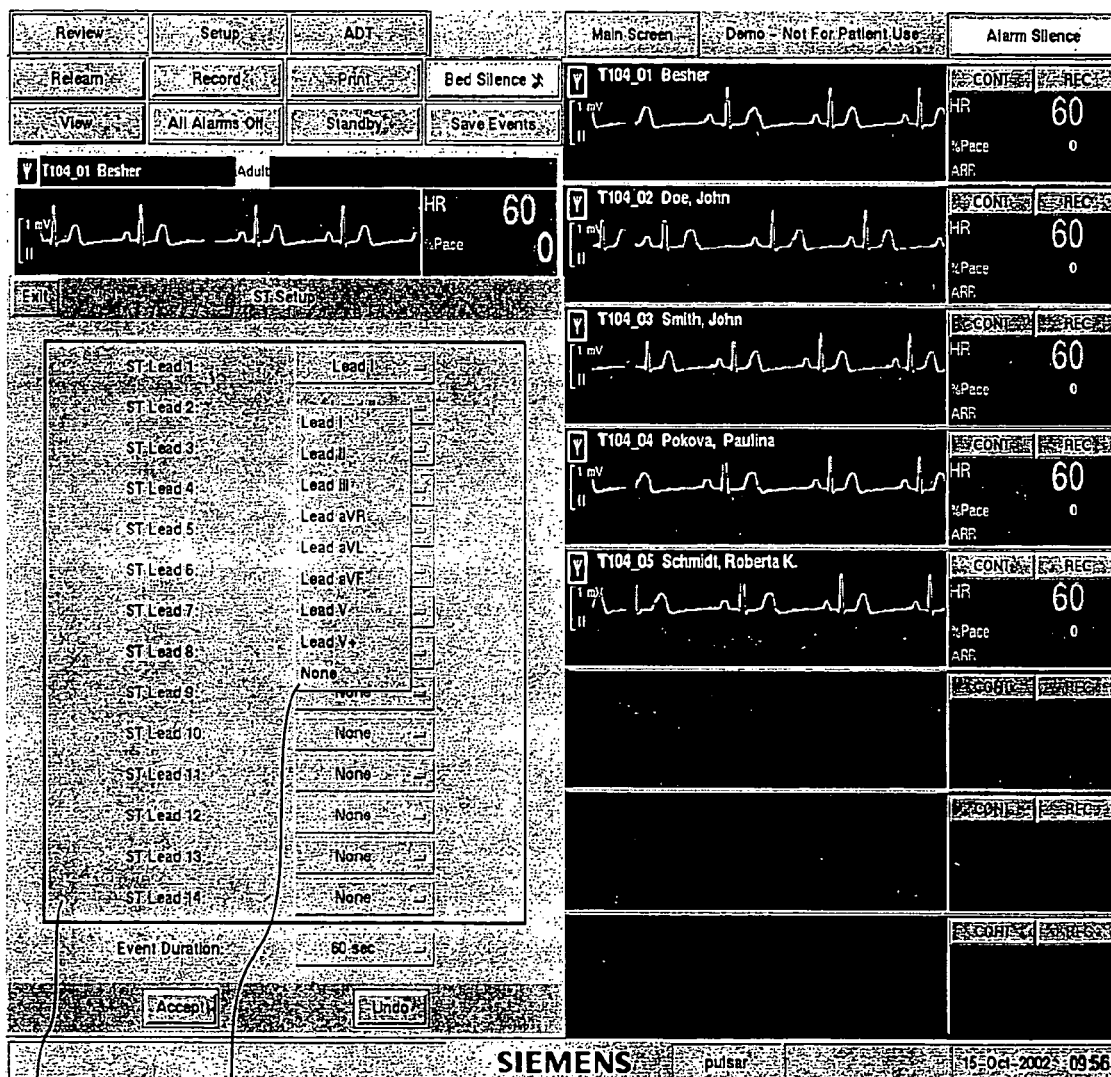

The user interface display image of FIG. 13 illustrates the configuration of the user interface image of FIG. 5 with synthesis mode selected to be off via item 405 thereby disabling synthesis of the four derived chest leads. In this non-synthesis mode labels and menus reflect the absence of derived chest lead signal information and indicate measurement chest lead signals are available. User selection of the non-synthesis mode results in inactivation of Set V and Set V+ function items 400 and 402 (shown ghosted) and the setting of chest lead labels (formerly V1 and V4 associated with display channels 2 and 8-column 430) in waveform column 434, back to V and V+, respectively. Pop-up menu 440 of FIG. 14 illustrates that available selectable labels comprise labels for measurement lead V and lead V+ instead of the chest lead labels that are available in synthesis mode. Similarly, menu 470 of FIG. 15 shows a set of updated labels for use in non-synthesis mode in determining an order of the ST parameters listed inside the windows 481 and 483 of the image of FIG. 10. Pop-up menu 472 of FIG. 16 illustrates a set of updated labels for use in associating an individual ECG lead signal with an individual ST parameter for use in non-synthesis mode. In non-synthesis mode, labels and menus reflect the absence of derived chest lead signal information and indicate measurement chest lead signals are available and show unused labels as being inactivated (and are shown ghosted). Consequently, the labels and menus are automatically updated in the user interface system images and menus (as illustrated in FIGS. 5–16) in response to user mode and setting selections.

In normal operation and in response to the user associating the two measurement chest leads V and V+ with correct chest electrodes V1 and V2, synthesizer 306 derives the remaining four chest lead signals V3, V4, V5, and V6. For this purpose controller 308 acquires the user entered information identifying the two measurement chest leads V and V+ as being coupled to chest electrodes V1 and V2. Controller 308 uses this identification information to identify and select coefficients from multiple sets of stored coefficients. The coefficients are advantageously used for any patient and are consequently patient non-specific. This means synthesizer 306 is able to quickly synthesize chest leads without requiring prior time consuming and complicated patient specific data accumulation for use in deriving patient specific transformation data to be used in synthesizing chest lead signals. In contrast, an alternative technique would involve recording at least some portion of a full 12 lead ECG for a particular patient, during an analysis phase. The recorded signals are processed to generate a patient specific function, which may be applied to lead signals which are available, to synthesize a lead signal which approximates a lead signal which is missing or distorted beyond use. During a synthesis phase, this patient specific function is applied to the available ECG lead signals. This alternative technique enables a missing lead to be synthesized for a particular patient but involves the disadvantages of being relatively complex and time consuming to perform.

Controller 308 selects coefficients (in a matrix arrangement, for example) associated with the identified measurement lead assignment (here V=V1 and V+=V2) from database 110. A user is able to associate the two measurement chest leads V and V+ with any two of the six chest electrodes V1–V6 and in any order i.e., V and V+ may be coupled with either V1 and V2 or V2 and V1 respectively. Therefore there are thirty different ways of associating V and V+ with two of the six chest electrodes V1–V6 and there are thirty corresponding sets (e.g., matrices) of coefficients stored in database 110 for use by synthesizer 306 in synthesizing the remaining four chest electrode signals. FIGS. 4a–4e show the thirty sets of patient non-specific coefficients in matrix form for use by synthesizer 306 in synthesizing the remaining four chest electrode signals. The thirty sets of patient non-specific coefficients comprise thirty different, four by four matrices each containing 16 coefficients.

A user is able to relocate either one or both of the two measurement chest leads from V1 and V2 in this exemplary operation description to a different one, or to a different pair, of chest electrodes respectively. As a result the two measurement electrodes are coupled to a selected different pair combination of chest electrodes. The user associates the two measurement chest leads V and V+ with the selected different pair combination of chest electrodes via menus displayed on screen 312 using controls 314. In response, controller 308 dynamically selects from database 110 a coefficient matrix corresponding to the selected different pair combination of electrodes.

Controller 308 retrieves the selected matrix of coefficients associated with the identified measurement lead assignment (here V=V1 and V+=V2) from database 110. Controller 308 inserts the selected matrix coefficients into matrix 307 memory locations in synthesizer 306. Synthesizer 306 employs the selected matrix coefficients 307 to synthesize the remaining four chest lead signals V3, V4, V5, and V6. For this purpose synthesizer 306 uses selected matrix coefficients 307 to perform a matrix multiplication comprising a linear transformation as indicated in FIG. 3. The matrix multiplication performed by synthesizer 306 derives data values representing the remaining four chest lead signals V3, V4, V5, and V6. This is done by multiplying the selected coefficient matrix 307 by an input matrix comprising data values of lead signals I and II (of the conventional 12 lead ECG signal set) as well as data values of the two measurement chest leads V and V+ as shown in FIG. 3. Lead signals I and II are computed from limb electrodes LA, RA, LL, and RL raw data as previously described and known. As indicated in FIG. 3, V3 is computed as:

$$V3 = C0,0*\text{Lead I} + C0,1*\text{Lead II} + C0,2*\text{Lead } V + C0,3*\text{Lead } V+$$

for example. Data values representing chest lead signals V4, V5 and V6 are similarly computed as shown in FIG. 3.

Synthesizer 306 applies the transformation of FIG. 3 to data values of lead signals I and II and V and V+ to derive data values representing V3, V4, V5 and V6. Thereby derived data representing signals V3–V6, together with measurement data representing V1 and V2 (from measurement leads V and V+), is available to provide a waveform display of the full set of chest lead signals V1–V6 on display screen 312 of display device 310. Chest lead signals V1–V6 are displayed on screen 312 together with lead signals I and II as well as signals III, aAR, aVL, and aVF (computed from lead signals I and II as known). As a result screen 312 displays the full conventional 12 lead ECG signal set.

Relocation of either one or both of the two measurement chest leads V and V+ to a selected different pair combination of chest electrodes, together with user association of the two measurement chest leads V and V+ with the selected different pair combination, via screen 312, automatically triggers controller 308 to initiate a fresh synthesis cycle. Specifically, controller 308 automatically selects from database 110 a coefficient matrix corresponding to the selected different pair combination of electrodes (e.g., V2 and V5) for incorporation in location 307 and initiates synthesis by synthesizer 306 of corresponding remaining electrode signals (e.g., V1, V3, V4 and V6) using the transformation of FIG. 3.

Figure 2:
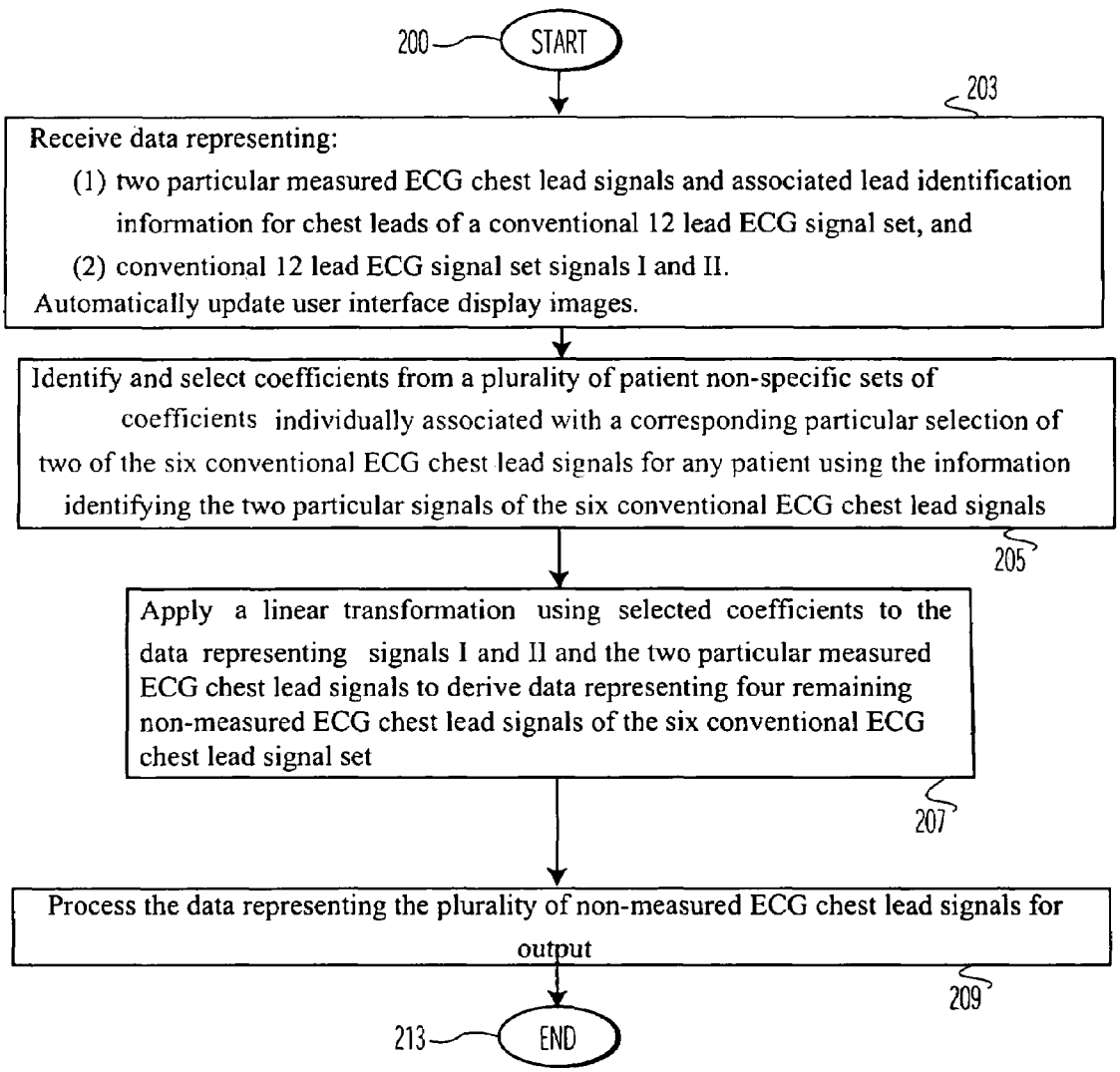
FIG. 2 is a flowchart of a process for adaptively deriving ECG chest lead signals used in the device of FIG. 1, according to principles of the present invention.

FIG. 2 is a flowchart of a process for adaptively deriving ECG chest lead signals used in the system of FIG. 1. After the start at step 200, preprocessor 104 provides synthesizer 306, in step 203, with digital data representing the two measurement chest leads V and V+ and digital data representing lead signals I and II. The user interface system automatically and dynamically updates ECG signal associated labels in multiple different waveform and parameter display images, windows and associated menus (exemplified in FIGS. 5–16) used for set-up and waveform and parameter display. This is done in response to user association of the two measurement chest leads V and V+ with particular chest electrodes identified by a user via user controls 314 (FIG. 1) using the displayed image windows. In step 205, controller 308 identifies and selects a set of coefficients from a plurality of stored patient non-specific sets of coefficients individually associated with a corresponding particular pair of electrodes. The coefficient sets (matrices in the preferred embodiment) are used for synthesizing (for any patient) up to four of the six ECG chest lead signals of the conventional 12 lead ECG set. Controller 308 selects the set of coefficients associated with the corresponding particular pair of electrodes in response to information identifying the particular two signals of the six conventional ECG chest lead signals entered by a user via user controls 314 (FIG. 1). In step 207 synthesizer 306 applies a transformation using the selected coefficients to digital data representing the two measurement chest lead signals V and V+ and lead signals I and II. This is done to derive data representing the four remaining non-measured ECG chest lead signals of the six ECG chest lead signals of the conventional 12 lead ECG set.

In step 209 controller 308 processes the derived and measured chest lead signal data as well as data representing lead signals I and II and signals III, aAR, aVL, and aVF (computed from lead signals I and II as known) for display on screen 312. Thereby screen 312 of display device 310 displays a full conventional 12 lead ECG signal set. The controller 308 also conditions the display device 310 to display an indication on the display screen 312 to alert the user that four of the displayed ECG chest lead signals are being synthesized, as previously explained in connection with the user interface display images of FIGS. 5–16. This indication is provided by placing measurement lead signal symbols V and V+ adjacent to the non-synthesized ECG chest waveforms and their associated chest lead signal identification symbols (e.g., symbols V1 and V2). The absence of V and V+ adjacent to the remaining four chest lead signals and identification symbols (e.g., V3, V4, V5 and V6) indicate that these are synthesized waveforms, as previously discussed. Alternatively, in other embodiments, synthesized waveforms may be indicated by highlighting the synthesized lead waveforms or the background of the synthesized lead waveforms, in some fashion, such as by varying the intensity or color of the synthesized lead waveforms relative to the other lead waveforms or by displaying a textual identification of the synthesized waveforms on the display screen 312. In another embodiment an alternative indicative symbol may be placed in the vicinity of the synthesized waveforms. The process of FIG. 2 terminates at step 213.

The user interface system and display images, coefficients and process presented in FIGS. 1–16 are not exclusive. Other systems, display images, coefficients and processes may be derived in accordance with the principles of the invention to accomplish the same objectives. Further, the inventive system as described herein in other embodiments may use a transformation other than a linear transformation which may include a polynomial or trigonometric function, for example. Although this invention has been described with reference to particular embodiments, it will be appreciated that many variations will be resorted to without departing from the spirit and scope of this invention as set forth in the appended claims. For example, the terms "controller" or "synthesizer" as used herein should be broadly construed to include any device capable of receiving, transmitting and/or using information including, without limitation, a processor, microprocessor or similar device, a personal computer, such as a laptop, palm PC, desktop, workstation, or word processor, a network server, a mainframe, an electronic wired or wireless device, such as for example, a telephone, an interactive television, such as for example, a television adapted to be connected to the Internet or an electronic device adapted for use with a television, a cellular telephone, a personal digital assistant, an electronic pager, a digital watch and the like. Further, a controller of the invention may operate in communication with other systems over a communication network, such as, for example, the Internet, an intranet, or an extranet, or may operate as a stand-alone system.

What is claimed is:

1. A user interface display system for use in ECG signal management, comprising:
    a display generator for generating at least one display image enabling assignment of two measured EGG chest lead signals to any two signals of the six EGG chest lead signals of a conventional 12 lead EGG signal set; and
    a command processor for automatically updating labels for identifying, (a) individual non-synthesized measured EGG chest lead signals and (b) individual synthesized non-measured EGG chest lead signals, associated with said six EGG chest lead signals displayed in a display image to be compatible with said assignment of said two measured EGG chest lead signals in response to an assignment command made via said at least one display image.

2. The system of claim 1 wherein
    said command processor automatically updates labels associated with said six EGG chest lead signals to identify two measured chest lead signals and four derived chest lead signals, in response to an assignment command made via said at least one display image.

3. The system of claim 1 wherein
    said two measured chest lead signals are the V and V+ lead signals of a conventional 12 lead EGG signal set.

4. The system of claim 1 wherein
    said command processor automatically updates labels associated with said six EGG chest lead signals to identify two measured chest lead signals and four derived chest lead signals in multiple display images including at least one of, (a) an EGG waveform display image, (b) a configuration screen for use in configuring a parameter display image for a particular patient and (c) a telemetry system configuration image, in response to an assignment command made via said at least one display image.

5. The system of claim 1 wherein
    said command processor automatically updates labels associated with said six ECG chest lead signals in a menu window used for assigning a particular chest lead EGG signal to a window used for displaying a corresponding particular chest lead EGG signal waveform.

6. The system of claim 1 wherein
    said command processor automatically updates labels associated with said six ECG chest lead signals in a menu window used for assigning a particular chest lead EGG signal to a display channel.

7. The system of claim 1 including
a data processor for, in a synthesis mode, identifying and selecting coefficients from a plurality of stored coefficients and applying a transformation, using said selected coefficients, to data comprising said two measured EGG chest lead signals to derive data representing a plurality of non-measured EGG chest lead signals and wherein
said command processor, in said synthesis mode automatically updates labels to identify individual synthesized non-measured EGG chest lead signals and individual non-synthesized measured EGG chest lead signals in response to said assignment command made via said at least one display image.

8. The system of claim 7 wherein
said command processor, in a non-synthesis mode, automatically updates labels to identify individual non-synthesized measured EGG chest lead signals.

9. The system of claim 8 wherein
said command processor, in said non-synthesis mode, automatically inactivates display items for use in associating measurement EGG chest leads with particular signals of the six chest lead signals of a conventional EGG signal set and updates menu labels to identify individual non-synthesized measured EGG chest lead signals and inactivate EGG chest lead signal labels associated with said synthesized mode.

10. The system of claim 9 wherein
said command processor inactivation of EGG chest lead signal labels comprises excluding said EGG chest lead signal labels associated with said synthesized mode.

11. The system of claim 1 wherein
said command processor automatically inactivates a label associated with an individual one of said six EGG chest lead signals in a second menu window in response to an assignment of said individual one of said six EGG chest lead signals to at least one of, (a) a display channel, (b) a display waveform, (c) a measured EGG chest lead signal and (d) a synthesized EGG chest lead signal, made via a first menu window.

12. The system of claim 1 wherein
said command processor automatically updates a label associated with ST parameter values of EGG waveform portions related to the S-Wave and T-Wave of at least one of said six EGG chest lead signals in response to said assignment command made via said at least one display image.

13. The system of claim 1 wherein
said command processor automatically updates labels associated with ST parameter values of EGG waveform portions related to the S-Wave and T-Wave of EGG signals in response to said assignment command made via said at least one display image.

14. A user interface display system for use in EGG signal management, comprising:
a display generator for generating at least one display image enabling assignment of measured EGG chest lead signals to signals of the six EGG chest lead signals of a conventional 12 lead EGG signal set; and
a command processor for,
in a synthesis mode, automatically updating labels associated with said six EGG chest lead signals displayed in at least one display image to identify individual synthesized non-measured EGG chest lead signals and individual non-synthesized measured EGG chest lead signals to be compatible with said assignment of said measured EGG chest lead signals in response to an assignment command made via said at least one display image.

15. The system of claim 14 wherein
said command processor, in a non-synthesis mode, automatically updates labels to identify individual non-synthesized measured EGG chest lead signals and at least one of, (a) inactivate and (b) exclude, EGG chest lead signal labels associated with said synthesized mode.

16. The system of claim 14 wherein
said command processor, in said non-synthesis mode, automatically inactivates display items for use in associating measurement EGG chest leads with particular signals of the six chest lead signals of a conventional EGG signal set.

17. The system of claim 14 including
a data processor for, in a synthesis mode, identifying and selecting coefficients from a plurality of stored coefficients and applying a transformation, using said selected coefficients, to said data comprising said measured EGG chest lead signals to derive data representing a plurality of non-measured EGG chest lead signals.

18. A user interface display system for use in EGG signal management, comprising:
a display generator for generating at least one display image enabling assignment of measured EGG chest lead signals to signals of the six EGG chest lead signals of a conventional 12 lead EGG signal set; and
a command processor for,
in a synthesis mode, automatically updating labels associated with said six EGG chest lead signals displayed in at least one display image to identify individual synthesized non-measured EGG chest lead signals and individual non-synthesized measured EGG chest lead signals to be compatible with said assignment of said measured EGG chest lead signals in response to an assignment command made via said at least one display image, and
in a non-synthesis mode, automatically updating labels to identify individual non-synthesized measured EGG chest lead signals and at least one of, (a) inactivate and (b) exclude, ECG chest lead signal labels associated with said synthesized mode.

19. The system of claim 18 wherein
said command processor automatically inactivates a label associated with an individual one of said six ECG chest lead signals in a second menu window in response to an assignment of said individual one of said six EGG chest lead signals to at least one of, (a) a display channel, (b) a display waveform, (c) a measured EGG chest lead signal and (d) a synthesized EGG chest lead signal, made via a first menu window.

20. A method for providing a user interface for use in EGG signal management, comprising the steps of:
generating at least one display image enabling assignment of two measured EGG chest lead signals to any two signals of the six EGG chest lead signals of a conventional 12 lead EGG signal set; and
automatically updating labels for identifying, (a) individual non-synthesized measured EGG chest lead signals and (b) individual synthesized non-measured EGG chest lead signals, associated with said six EGG chest lead signals displayed in a display image to be compatible with said assignment of said two measured EGG chest lead signals in response to an assignment command made via said at least one display image.

21. A method for providing a user interface for use in EGG signal management, comprising the steps of:

generating at least one display image enabling assignment of measured EGG chest lead signals to signals of the six EGG chest lead signals of a conventional 12 lead EGG signal set; and automatically updating, in a synthesis mode, labels associated with said six EGG chest lead signals displayed in at least one display image to identify individual synthesized non-measured EGG chest lead signals and individual non-synthesized measured EGG chest lead signals to be compatible with said assignment of said measured EGG chest lead signals in response to an assignment command made via said at least one display image.

22. A user interface display system for use in EGG signal management, comprising:

a display generator for generating at least one display image enabling assignment of two measured EGG chest lead signals to any two signals of the six EGG chest lead signals of a conventional 12 lead EGG signal set; and a command processor for automatically updating labels for identifying individual synthesized non-measured EGG chest lead signals associated with said six EGG chest lead signals displayed in a display image to be compatible with said assignment of said two measured EGG chest lead signals in response to an assignment command made via said at least one display image.

* * * * *